(12) United States Patent
Lin et al.

(10) Patent No.: US 6,733,504 B2
(45) Date of Patent: May 11, 2004

(54) CERVICAL DOWEL AND INSERTION TOOL

(75) Inventors: Ching-Yi Lin, Fort Lee, NJ (US); Jo-Wen Lin, Titon Falls, NJ (US)

(73) Assignee: Osteotech, Inc., Eatontown, NJ (US)

( * ) Notice: Subject to any disclaimer, the term of this patent is extended or adjusted under 35 U.S.C. 154(b) by 307 days.

(21) Appl. No.: 09/992,473

(22) Filed: Nov. 16, 2001

(65) Prior Publication Data

US 2002/0116008 A1 Aug. 22, 2002

Related U.S. Application Data (62) Division of application No. 09/685,530, filed on Oct. 10, 2000, now Pat. No. 6,527,773.
(60) Provisional application No. 60/158,074, filed on Oct. 7, 1999.

(51) Int. Cl.$^7$ .................................................. A61F 2/46
(52) U.S. Cl. ........................ 606/99; 606/104; 606/61; 623/17.11
(58) Field of Search ........................ 606/104, 61, 99; 81/176.1, 176.15, 176.2, 176.3, 443, 445; 623/17.11, 17.16

(56) References Cited

U.S. PATENT DOCUMENTS

| | | | |
|---|---|---|---|
| 2,525,222 A | * | 10/1950 | Holt ........................ 81/176.15 |
| 3,486,505 A | | 12/1969 | Morrison |
| 3,604,487 A | * | 9/1971 | Gilbert ........................ 81/443 |
| 3,848,601 A | | 11/1974 | Ma et al. |
| 4,349,921 A | | 9/1982 | Kuntz |
| 4,566,466 A | | 1/1986 | Ripple et al. |
| 4,743,256 A | | 5/1988 | Brantigan |
| 4,753,235 A | | 6/1988 | Hasson |
| 4,877,020 A | | 10/1989 | Vich |
| 4,955,885 A | | 9/1990 | Meyers |
| 5,192,327 A | | 3/1993 | Brantigan |
| 5,423,825 A | | 6/1995 | Levine |
| 5,443,514 A | | 8/1995 | Steffee |
| 5,707,371 A | | 1/1998 | Metz-Stavenhagen |
| 5,716,415 A | | 2/1998 | Steffee |
| 5,720,751 A | | 2/1998 | Jackson |
| 5,776,199 A | | 7/1998 | Michelson |
| 5,782,830 A | | 7/1998 | Farris |
| 5,885,299 A | * | 3/1999 | Winslow et al. ............... 606/99 |
| 5,885,300 A | | 3/1999 | Tokuhashi et al. |
| 6,066,174 A | | 5/2000 | Farris |
| 6,083,225 A | | 7/2000 | Winslow et al. |
| 6,159,215 A | | 12/2000 | Urbahns et al. |

OTHER PUBLICATIONS

Jose M. Otero Vich, M.D., Anterior cervical interbody fusion with threaded cylindrical bone, J. Neurosurg 63:750–753, 1985.

* cited by examiner

*Primary Examiner*—Julian W. Woo
(74) *Attorney, Agent, or Firm*—Dilworth & Barrese, LLP (57) ABSTRACT

A dowel insertion tool includes a T-shaped handle and a hollow sleeve which extends distally from the T-shaped handle. A shaft extends from the handle through the hollow sleeve and includes a transverse extension. A rotatable knob having an annular channel positioned to receive the transverse extension is supported adjacent the handle. A pin is secured to the knob and extends into a helical camming channel formed in the sleeve. Upon rotation of the knob, the pin moves within the camming channel to move the knob longitudinally about the sleeve. Movement of the knob effects longitudinal movement of the shaft. A support plate is secured to the distal end of the shaft. A pair of prongs are slidably secured to the plate. Each of the prongs includes an enlarged head portion which is slidably positioned within a slot formed in the plate. A guide member is secured to the distal end of the sleeve. The guide member includes a pair of guide bores dimensioned to receive a distal end of the prongs. The guide bores direct the prongs outwardly from the distal end of the hollow sleeve at an angle to the longitudinal axis of the sleeve. The prongs are dimensioned to be received in bores formed in the trailing end of a cervical dowel. Because the prongs engage the dowel at an angle, the dowel is both rotatably and longitudinally fixed to the insertion tool.

10 Claims, 15 Drawing Sheets

CERVICAL DOWEL AND INSERTION TOOL

This application is a divisional of U.S. application Ser. No. 09/685,530 filed on Oct. 10, 2000 U.S. Pat. No. 6,527,773. This application also claims priority from U.S. provisional application Serial No. 60/158,074, filed Oct. 7, 1999. Both of the above applications are incorporated herein by reference.

BACKGROUND

1. Technical Field

The present disclosure relates generally to surgical implants and to implant insertion tools and, more specifically, to cervical dowels and an insertion tool for inserting a cervical dowel into a receiving bed formed in an intervertebral space.

2. Background of Related Art

Cervical dowels and tools for inserting cervical dowels into the intervertebral space are well known in the prior art. For Example, U.S. Pat. No. 4,877,020 to which discloses a bone dowel and an instrument for inserting the bone dowel into the cervical region of the spine. The Vich dowel includes a cylindrical body, which is formed of bone extracted from the patient'siliac crest. A coil or thread is formed about the exterior surface of the dowel and the dowel is screwed into a previously prepared bed in the intervertebral space. Vich discloses a pair of instruments for inserting the dowel into the intervertebral space. A first instrument includes a pair of pins and a centrally located screw. The screw and pins penetrate one end of the dowel to secure the dowel onto a distal end of the insertion tool. Vich also discloses an insertion tool having an expandable sleeve portion which is positioned over one end of the dowel and clamped down to secure the dowel to the insertion tool.

Vich's insertion tools are lacking in several respects. For example, Vich's screw/pin insertion tool requires that the dowel be screwed onto the insertion tool. This makes it difficult and time consuming for a surgeon to disengage the dowel from the insertion tool. Moreover, Vich's expandable sleeve insertion tool has a diameter larger than diameter of the dowel. Thus, it is very difficult using this insertion tool to fully insert a dowel into the intervertebral space.

Accordingly, a continuing need exists for a dowel insertion tool which can be quickly and easily attached and detached to/from a bone dowel. Moreover, a continuing need exists for an insertion tool which does not interfere with dowel insertion into the intervertebral space.

SUMMARY

In accordance with the present disclosure, a dowel and a dowel insertion tool for inserting the dowel into the intervertebral space are provided. The implant insertion tool includes a T-shaped handle having a hollow sleeve which extends from the T-shaped handle. A shaft extends from the handle through the sleeve and includes a transverse extension. A rotatable knob having an annular channel positioned to receive the transverse extension is supported adjacent the handle. A pin is secured to the knob and extends into a helical camming channel formed in the sleeve.

Upon rotation of the knob, the pin moves within the camming channel to move the knob longitudinally about the sleeve. Movement of the knob effects longitudinal movement of the shaft. A plate is secured to the distal end of the shaft. A pair of prongs are slidably secured to the plate. Each of the prongs includes an enlarged head portion which is slidably positioned within a slot formed in the plate. A guide member is secured to the distal end of the sleeve. The guide member includes a pair of guide bores which direct the prongs away from the sleeve at an angle to the longitudinal axis of the sleeve. The prongs are dimensioned to be received in bores formed in the trailing end of a cervical dowel. Because the prongs engage the dowel at an angle, the dowel is both rotatably and longitudinally fixed to the insertion tool.

BRIEF DESCRIPTION OF THE DRAWINGS

Preferred embodiments of the presently disclosed dowel insertion tool and associated dowels are described herein with reference to the drawings, wherein.

FIGS. 17–20 illustrate an insertion tool 200 for engaging and releasably securing dowel 100 to a distal end thereof. Briefly, insertion tool 200 includes a T-handle 210 having a hollow sleeve 212 extending therefrom. A shaft 214 extends from a proximal end of sleeve 212 to the distal end of sleeve 212. The proximal end of shaft 214 has a transverse extension 216. A rotatable knob 218 includes an annular channel (not shown) formed on its internal surface. Knob 218 is positioned about shaft 214 such that transverse extension 216 is positioned in the annular channel. A pin 217 is secured to knob 218 and extends into a camming channel (not shown), e.g., helical channel, formed in sleeve 212. Upon rotation of knob 218, pin 217 moves within the camming channel formed in sleeve 212 to move knob 218 longitudinally about sleeve 212. Movement of knob 212 causes corresponding longitudinal movement of shaft 214. A plate 220 is secured to the distal end of shaft 214. A pair of prongs 222 are slidably secured to plate 220. Each of the prongs 222 includes an enlarged head portion 224 and an elongated body portion 226. Each head portion 224 is slidably positioned within a respective slot 228 formed in plate 220. A guide member 230 is secured to the distal end of sleeve 212. Guide member 230 includes a pair of guide bores 232 which guide and direct prongs 222 at an angle to the longitudinal axis guide sleeve 1212 into bores 106 of dowel 100.

Figure 1:
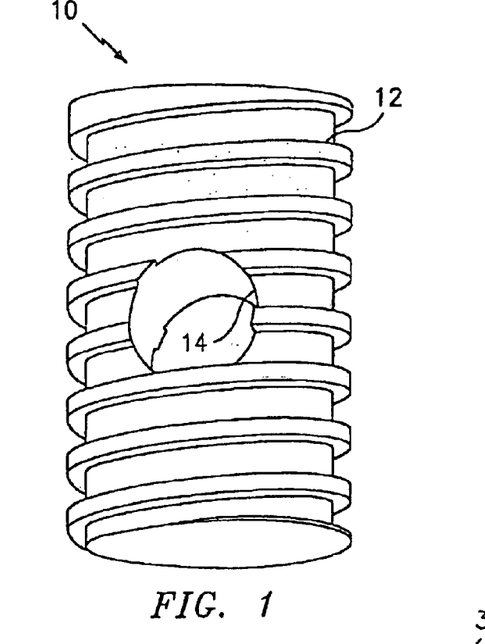
FIG. 1 is a perspective view of one embodiment of the presently disclosed cervical bone dowel.
Figure 2:
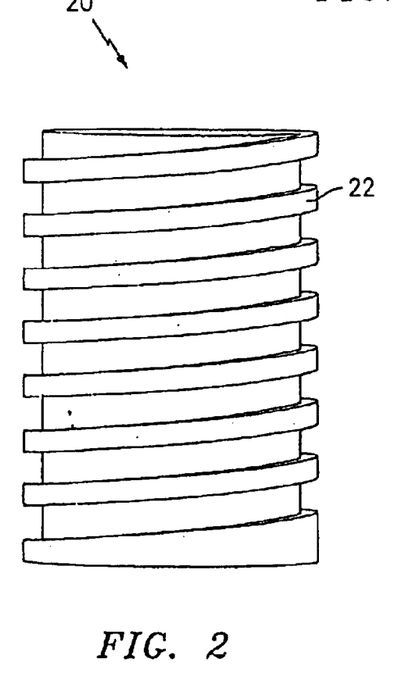
FIG. 2 is a side elevational view of another embodiment of the presently disclosed cervical bone dowel.
Figure 3:
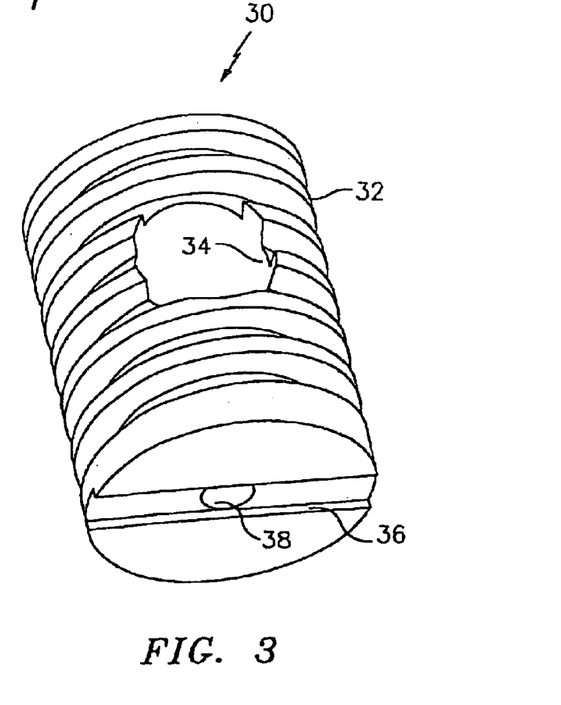
FIG. 3 is a perspective view of another embodiment of the presently disclosed cervical bone dowel.
Figure 4:
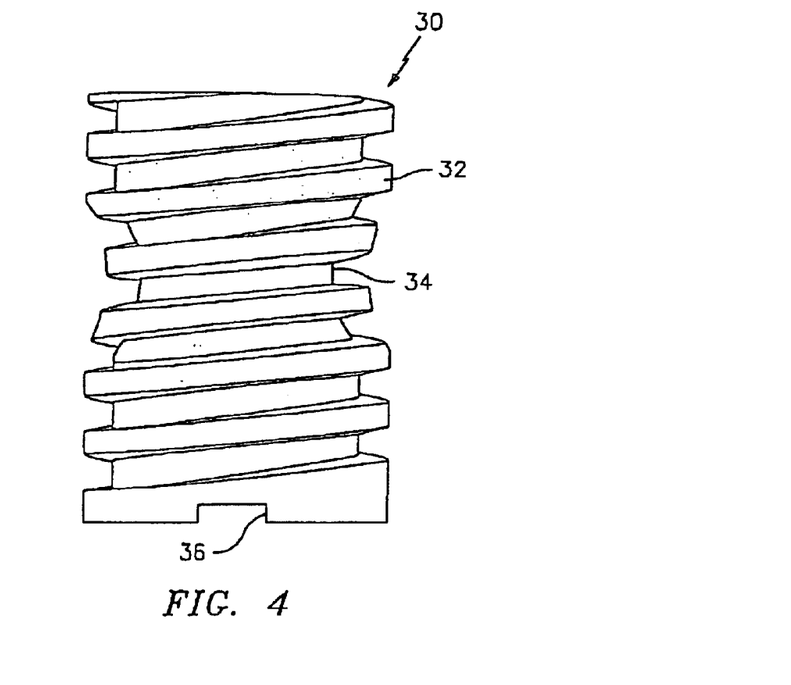
FIG. 4 is a side elevational view of the cervical bone dowel shown in FIG. 3.
Figure 5:
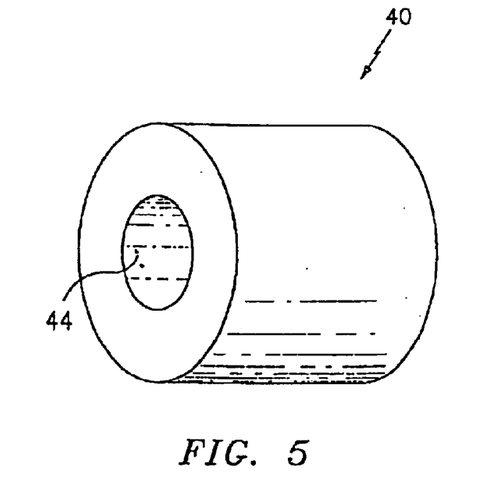
FIG. 5 is a perspective view of yet another embodiment of the presently disclosed cervical bone dowel.
Figure 6:
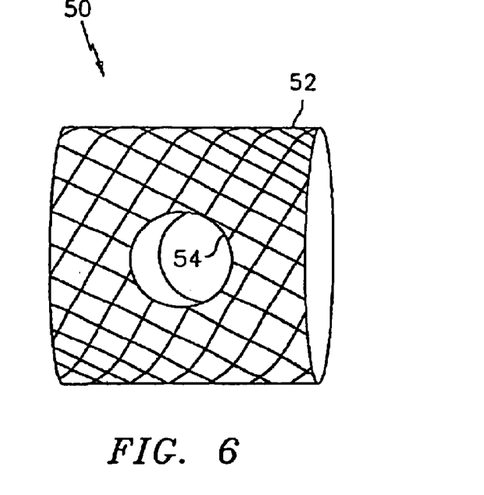
FIG. 6 is a perspective view of yet another embodiment of the presently disclosed cervical bone dowel.
Figure 7:
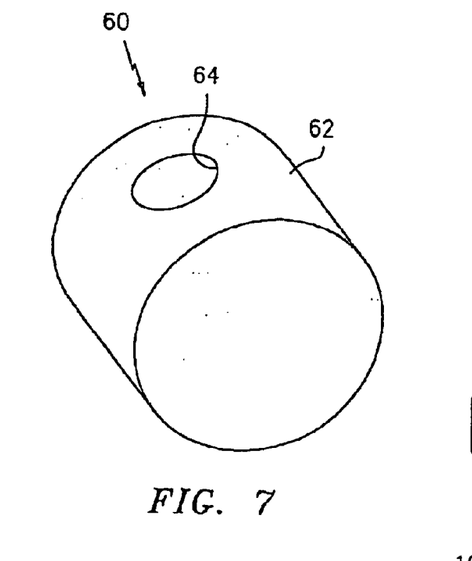
FIG. 7 is a perspective view of yet another embodiment of the presently disclosed cervical bone dowel.
Figure 8:
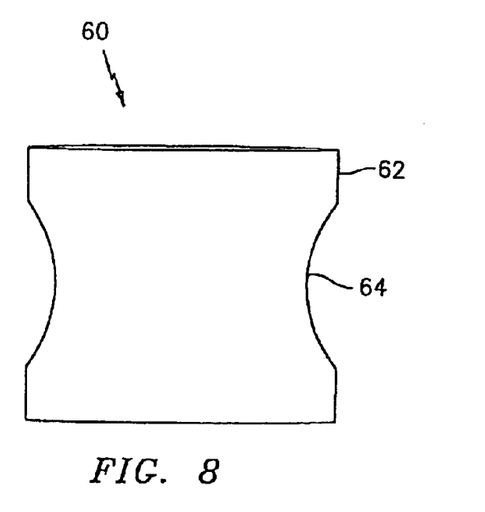
FIG. 8 is a side elevational view of the cervical bone dowel shown in FIG. 7.
Figure 9:
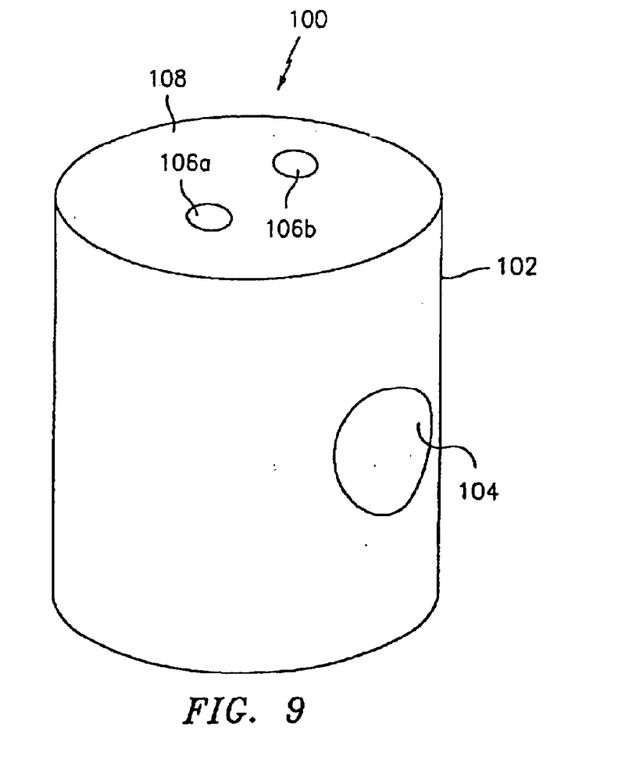
FIG. 9 is a perspective view of yet another embodiment of the presently disclosed cervical bone dowel.
Figure 10:
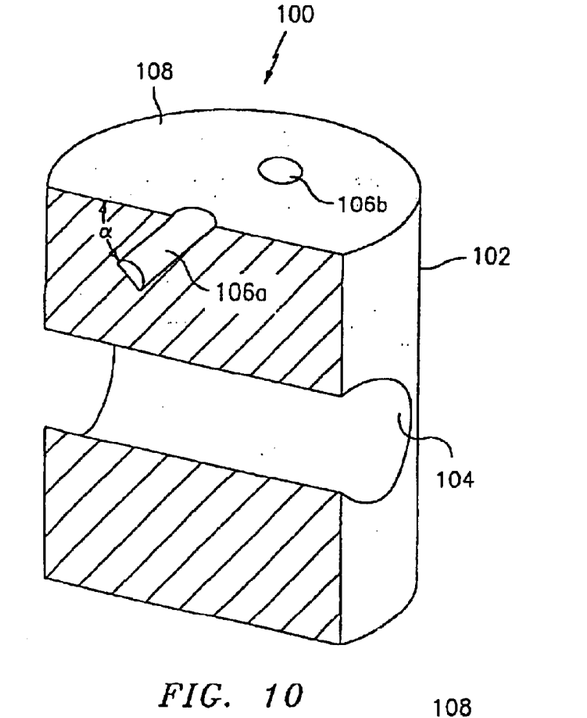
FIG. 10 is a side cross-sectional view of the cervical bone dowel shown in FIG. 9.
Figure 11:
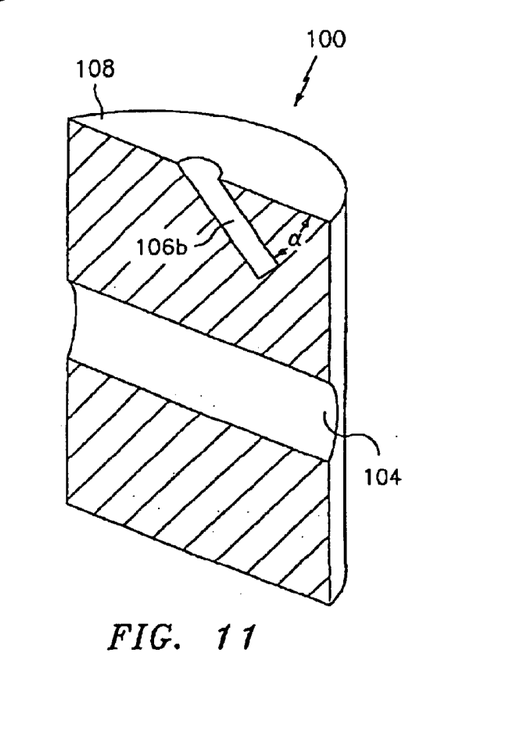
FIG. 11 is a side cross-sectional view of the cervical bone dowel shown in FIG. 9.
Figure 12:
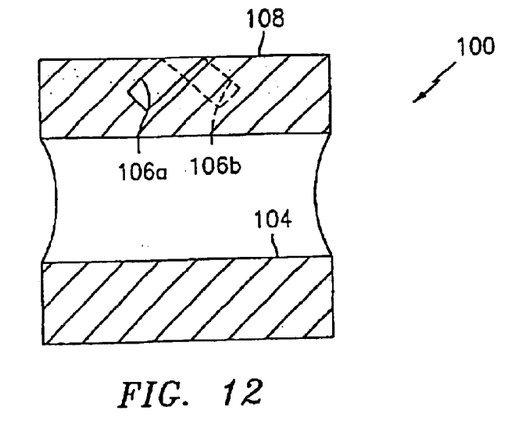
FIG. 12 is a side cross-sectional view of the cervical bone dowel shown in FIG. 9.
Figure 13:
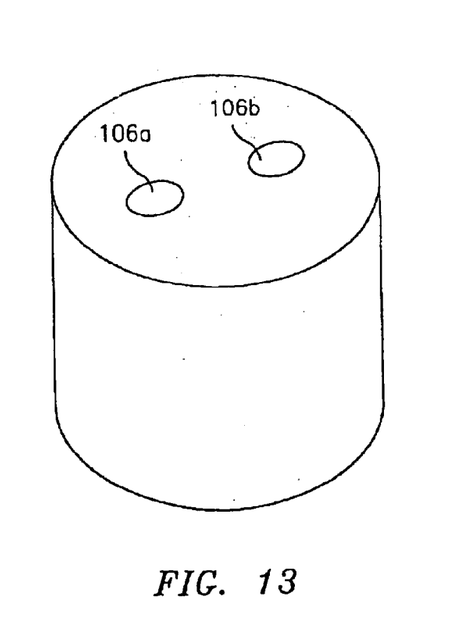
FIG. 13 is a perspective view of yet another embodiment of the presently disclosed cervical bone dowel.
Figure 14:
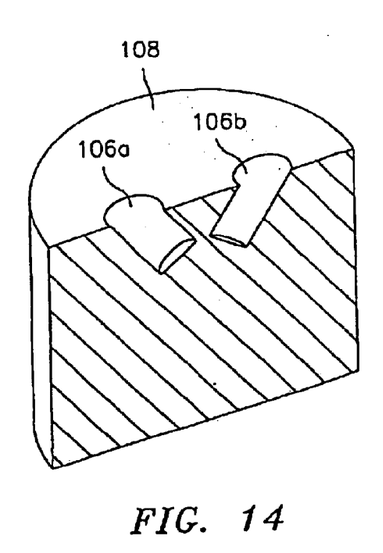
FIG. 14 is a side cross-sectional view of the cervical bone dowel shown in FIG. 13.
Figure 15:
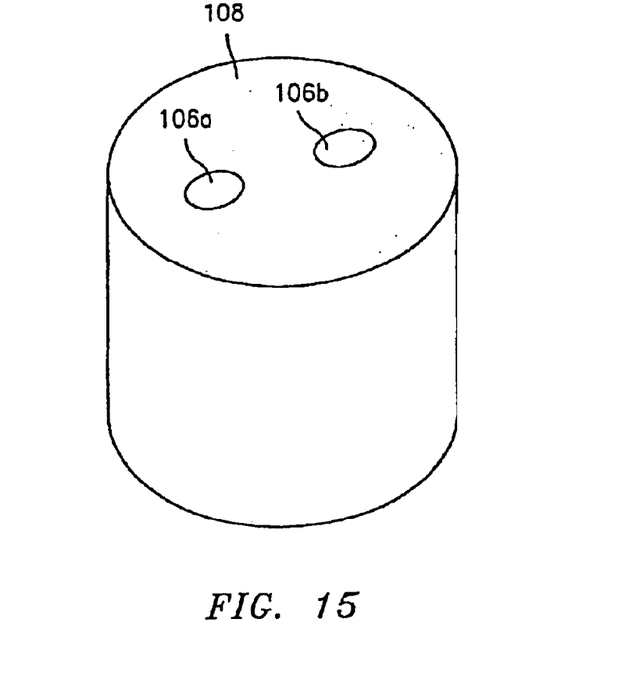
FIG. 15 is a perspective view of yet another embodiment of the presently disclosed cervical bone dowel.
Figure 16:
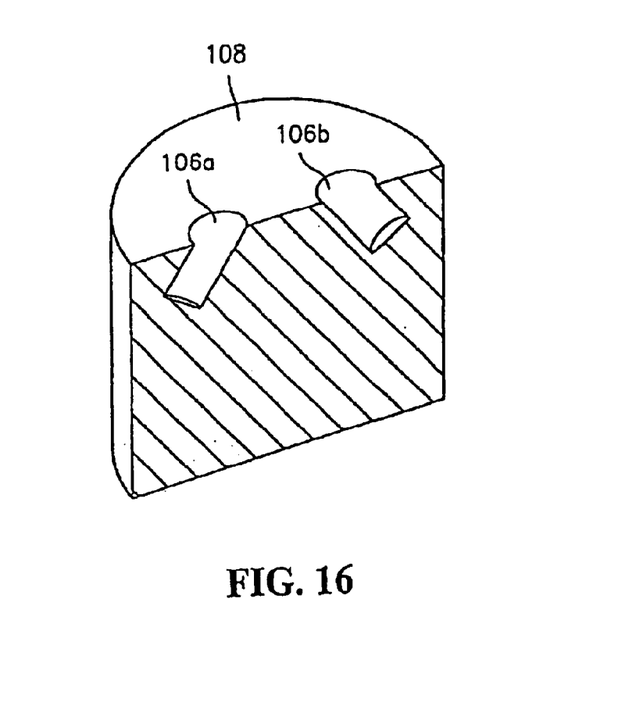
FIG. 16 is a side cross-sectional view of the cervical bone dowel shown in FIG. 15.
Figure 17:
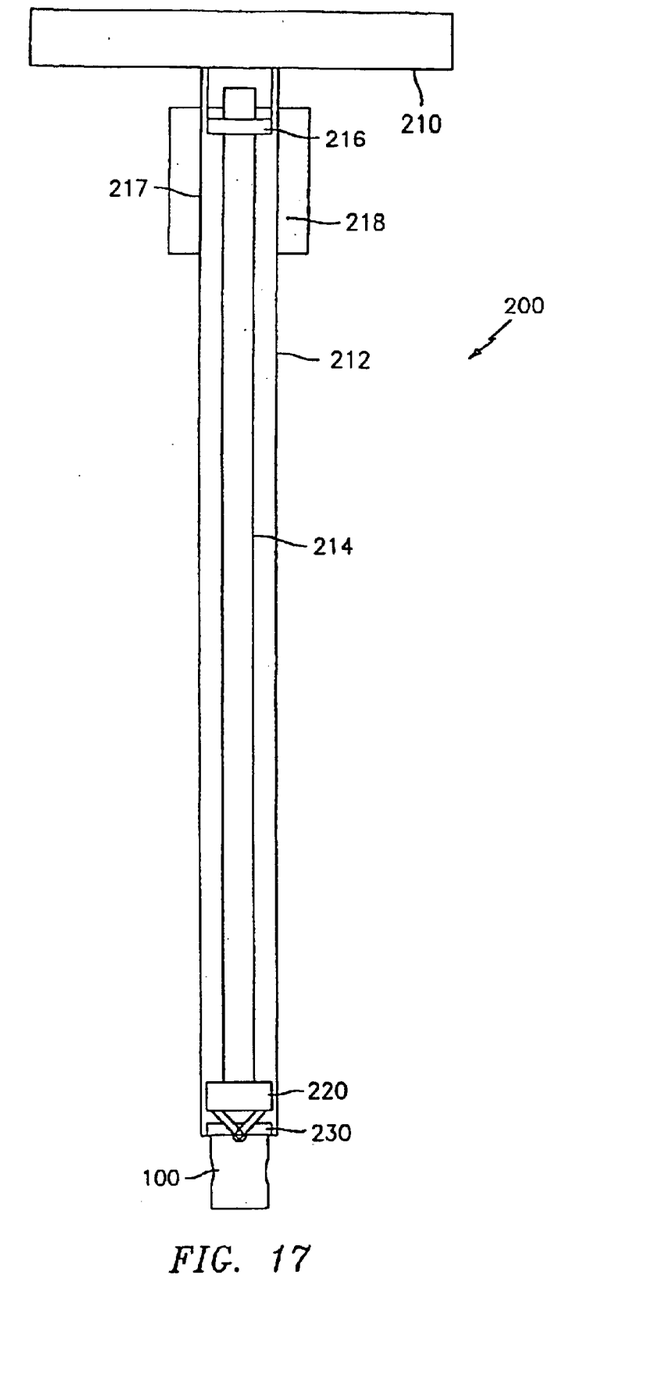
FIG. 17 is a side elevational view of one embodiment of the presently disclosed dowel insertion tool with a bone dowel secured to a distal end thereof.
Figure 18:
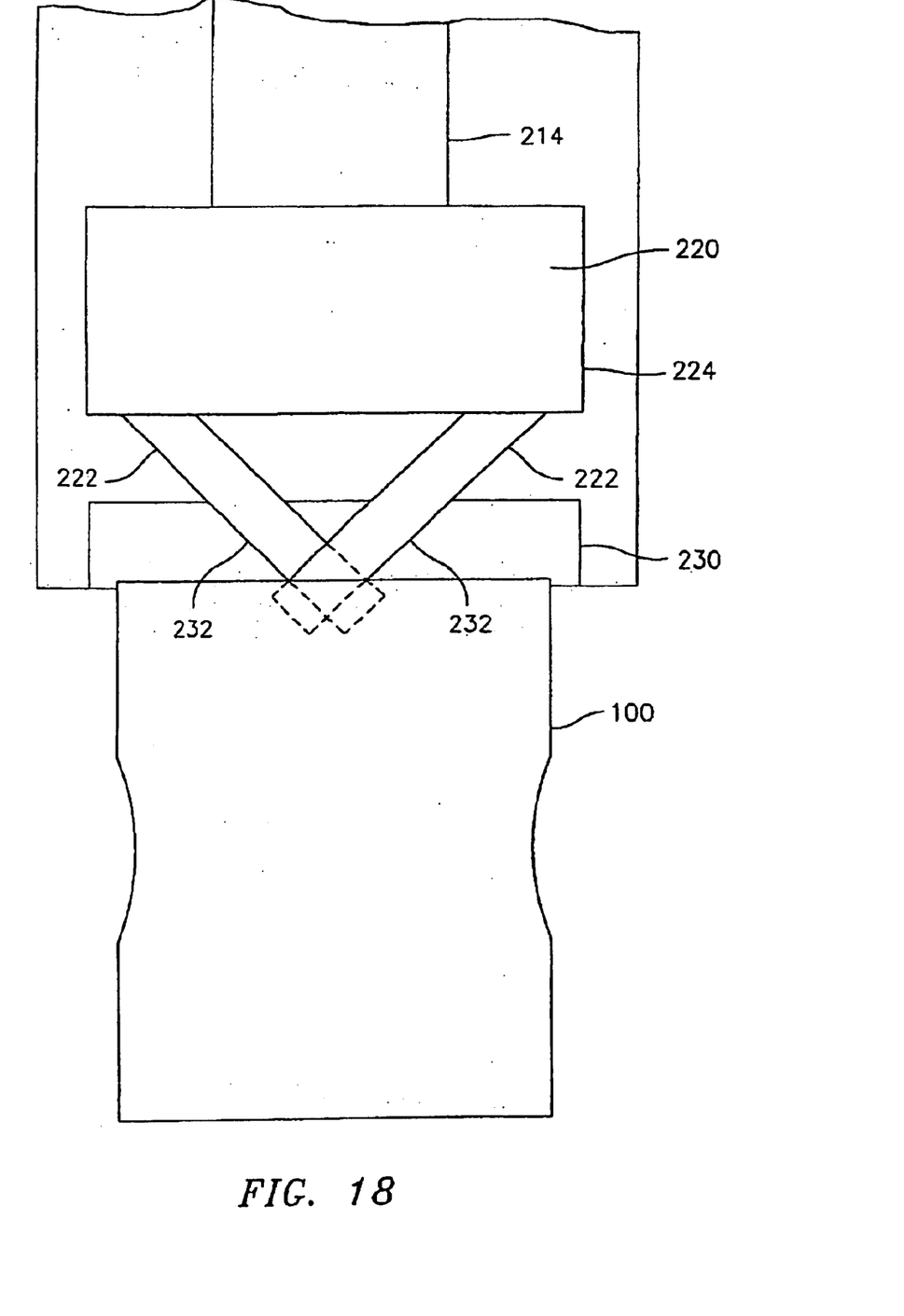
FIG. 18 is an enlarged partial cutaway view of the distal end of the insertion tool shown in FIG. 17.
Figure 19:
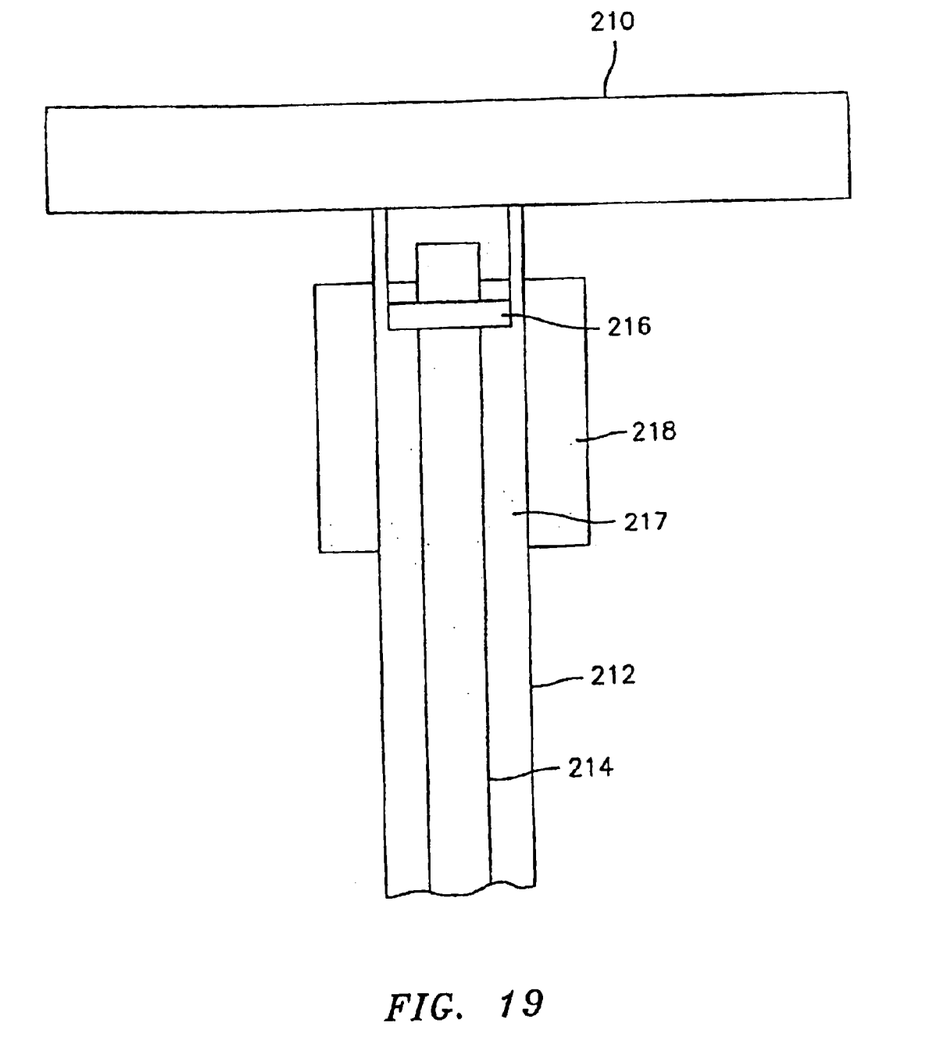
FIG. 19 is an enlarged partial cutaway view of the proximal end of the insertion instrument shown in FIG. 1.
Figure 20:
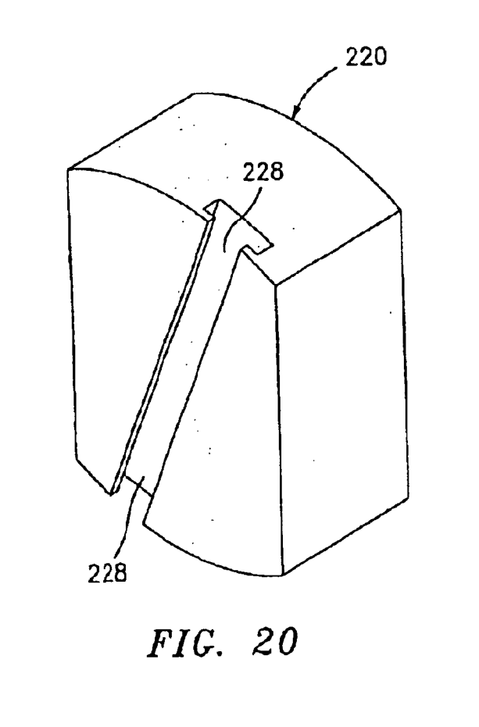
FIG. 20 is a perspective view from the front end of the prong support plate of the insertion tool shown in FIG. 17.
Figure 21:
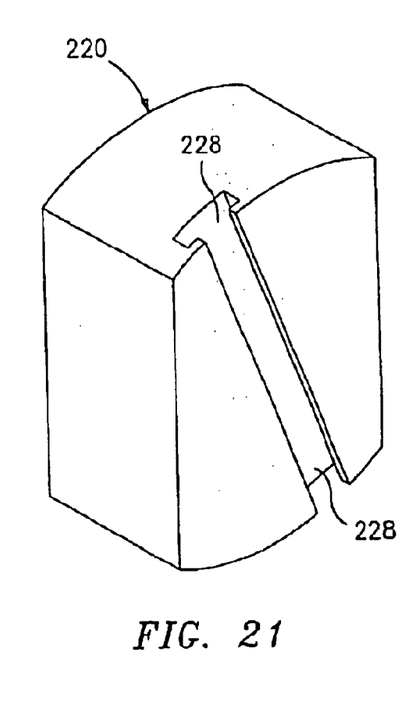
FIG. 21 is another perspective view from the front end of the prong support plate of the insertion tool shown in FIG. 17.
Figure 22:
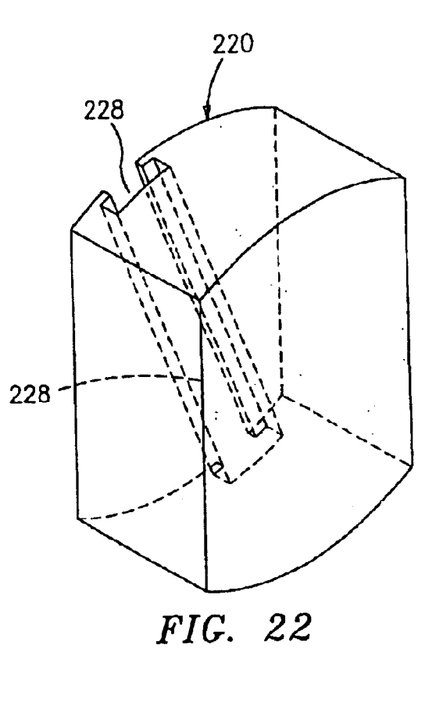
FIG. 22 is yet another perspective from the front end of the prong support plate of the insertion tool shown in FIG. 17.
Figure 23:
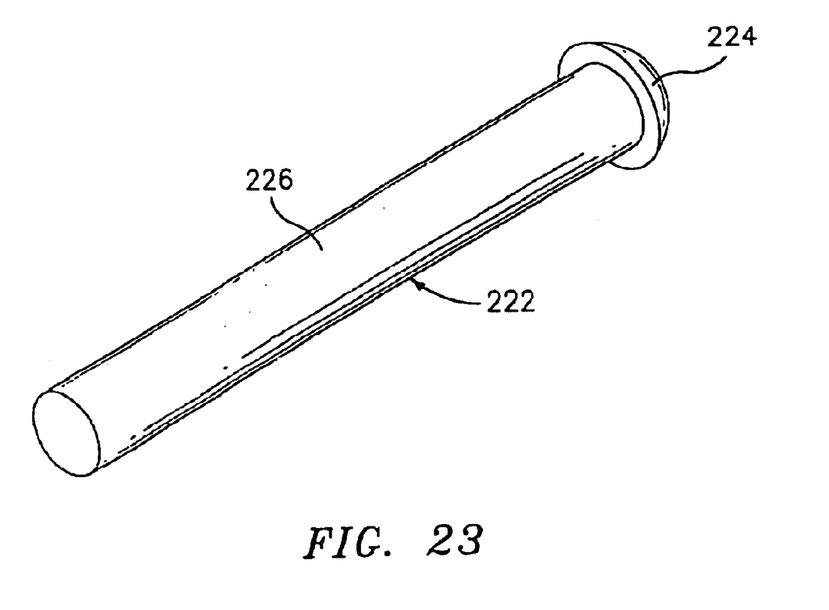
FIG. 23 is a perspective view of a prong of the insertion tool shown in FIG. 17.
Figure 24:
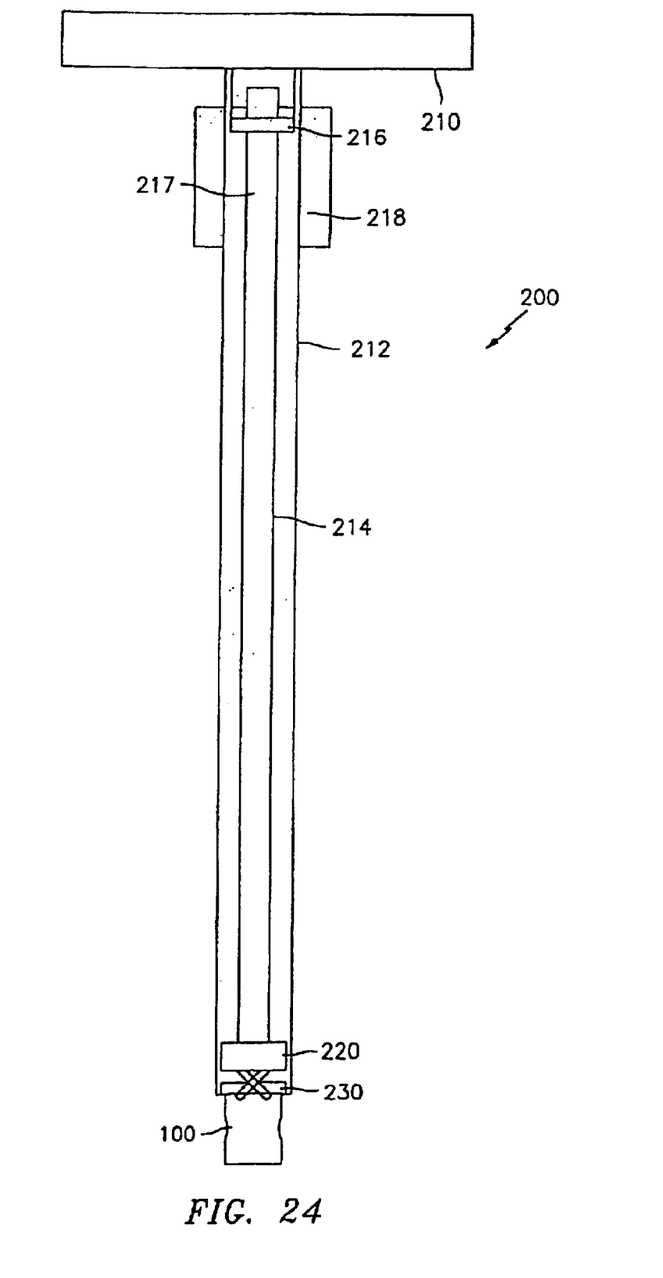
FIG. 24 is a side elevational view of the dowel insertion tool shown in FIG. 17 with the prongs in a partially advanced state; in a common vertical plane (FIGS. 13 and 14) or bores 106a and 106b may diverge from each other in a common vertical plane (FIGS. 15 and 16). Moreover, the angle of bores 106 may vary substantially from that illustrated. For example, the angle of bores 106 with respect to the plane defined by end surface 108 of dowel 100 may be approximately 15°, 75°,60° etc.
Figure 25:
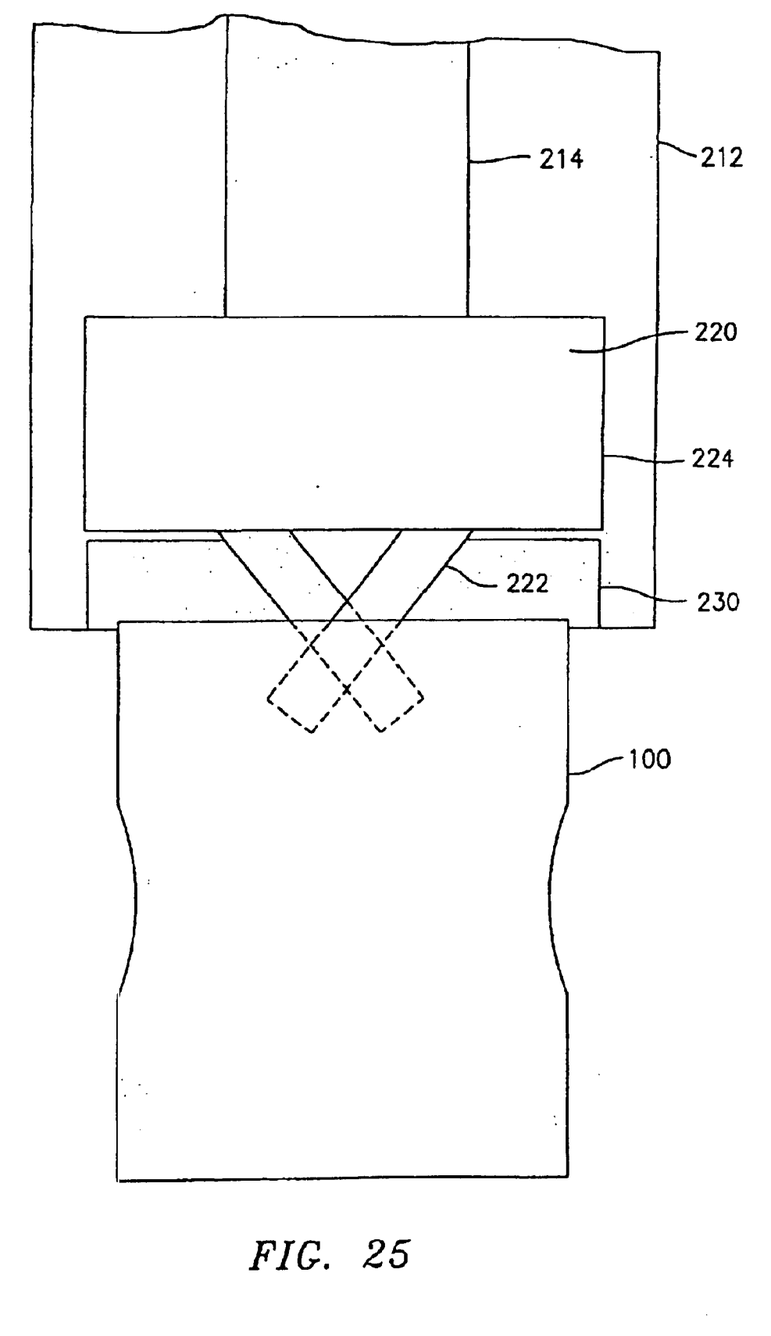

Referring to FIGS. 24 and 25, in use, a dowel 100 is positioned adjacent the distal end of sleeve 212 and knob 218 is rotated to advance shaft 214 within sleeve 212. As shaft 214 is advanced, plate 220 is advanced towards guide member 230 to advance prongs 222 through guide bores 232 and into engaging bores 106a and 106b of dowel 100. Because the angle of guide bores 232 and engaging bores 106a and 106b are fixed, each head portion 224 is forced to slide within a respective slot 228 of plate 220 as plate 220 approaches guide member 230. Because the insertion prongs 222 extend at a fixed angle through dowel 100, dowel 100 is both rotatably and longitudinally fixed with respect to the distal end of insertion tool 200. Thus, tool 200 can be rotated to apply a torque to dowel 100 or pushed/pulled to move dowel 100 longitudinally.

Figure 26:
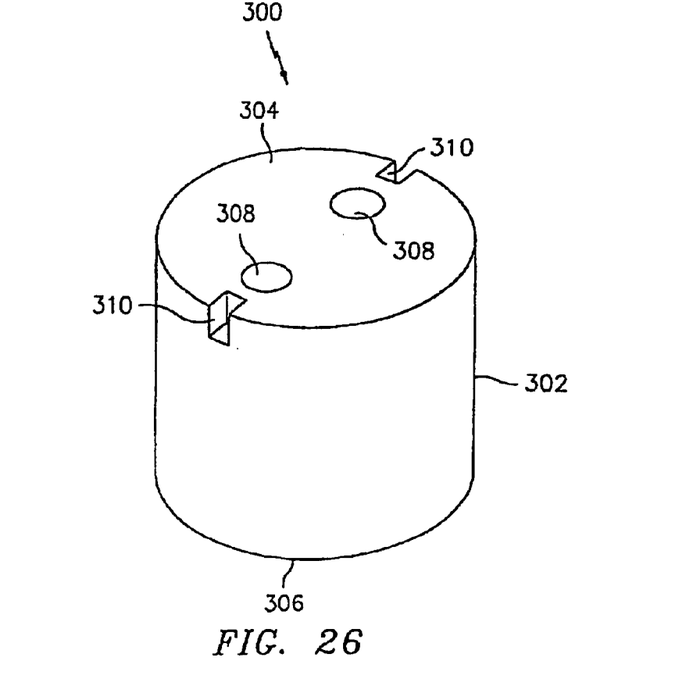
Figure 27:
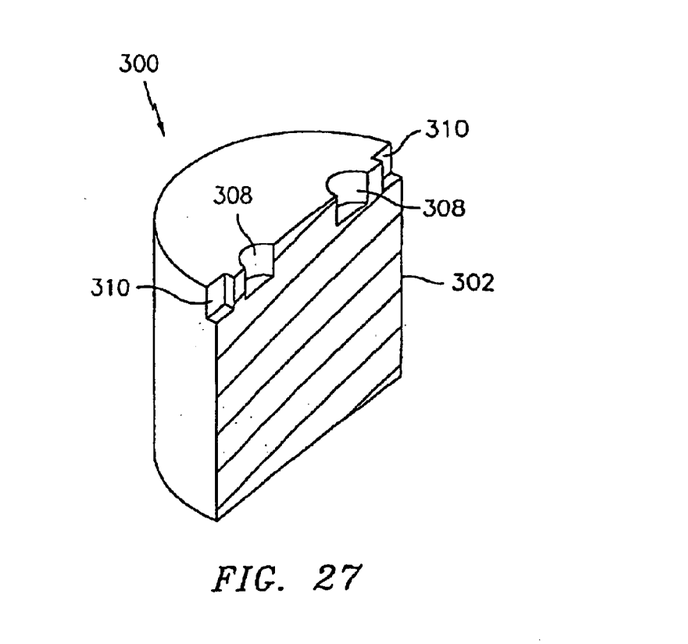

FIGS. 26 and 27 illustrate an alternate embodiment of the intervertebral dowel shown generally as 300. Dowel 300 includes a cylindrical body 302 having a first end face 304 and a second end face 306. A pair of holes 308 are formed in first end face 304 at locations spaced from the central axis of dowel 300. A pair of slots 310 are formed in the outer periphery of first end face 304. Slots 310 are positioned such that they extend along a portion of the outer cylindrical surface of dowel 300. Holes 306 are dimensioned and configured to receive insertion tool prongs to facilitate torquing of the dowel. Slots 310 are configured and dimensioned to receive clamping arms of a clamping mechanism (not shown) to secure dowel 300 to an insertion tool (not shown).

Figure 28:
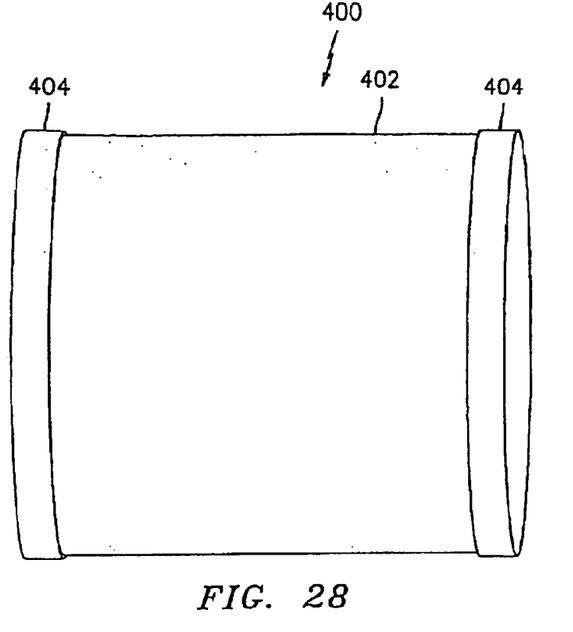
Figure 29:
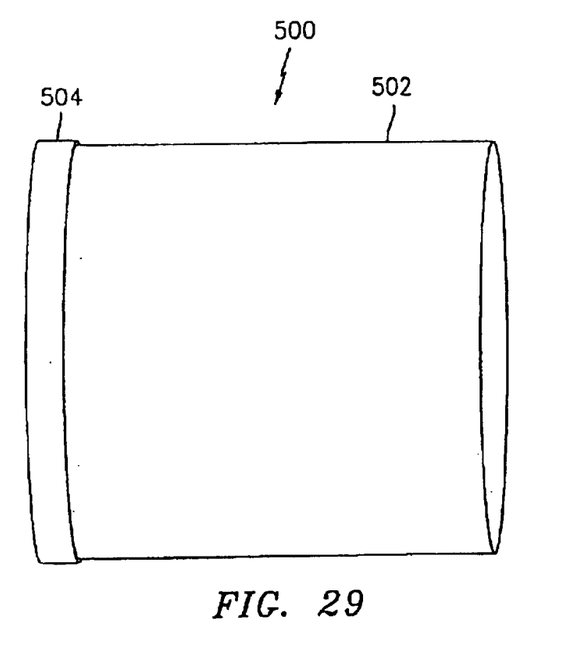

FIGS. 28 and 29 illustrate other alternate embodiments of the intervertebral dowel shown generally as 400 (FIG. 28) and 500. Dowel 400 includes a cylindrical body portion 402 formed from cancellous bone and opposite end portion 404 formed from cortical bone. Dowel 500 includes a cylindrical body portion 502 formed from cancellous bone and a single end portion 504 formed from cortical bone. Alternately, the entire dowel may be formed from cortical or cancellous bone.

It will be understood that various modifications may be made to the embodiments disclosed herein. For example, the particular angle of the prongs may vary. Moreover, the dowels may be formed from a variety of biocompatible materials. Therefore, the above description should not be construed as limiting, but merely as exemplifications of preferred embodiments. Those skilled in the art will envision other modifications within the scope and spirit of the claims appended hereto.

What is claimed:

1. A dowel insertion tool comprising:

a handle;

a hollow sleeve extending from the handle;

an elongated shaft extending through the hollow sleeve;

a knob rotatably secured about the hollow sleeve and being operably connected to the elongated shaft;

a support member positioned on a distal end of the elongated shaft; and at least one prong secured to the support member, the knob being rotatable to advance the elongated shaft within the hollow sleeve to advance the at least one prong from a position located substantially within the hollow sleeve to a position extending from the distal end of the hollow sleeve.

2. A dowel insertion tool comprising:

a handle;

a hollow sleeve defining a longitudinal axis, the hollow sleeve having a first end operably connected to the handle and a second end spaced from the handle;

an elongated member positioned within the hollow sleeve, the elongated member having a first end and a second end;

an actuator operably connected to the first end of the elongated member; and at least one prong operably connected to the second end of the elongated member;

wherein the actuator is operable to move the elongated member between a retracted position in which the at least one prong is located substantially within the hollow sleeve, and an advanced position in which the at least one prong extends from the second end of the hollow sleeve.

3. A dowel insertion tool according to claim 2, wherein in the advanced position, the at least one prong has a longitudinal axis which extends orthogonally to the longitudinal axis of the hollow sleeve.

4. A dowel insertion tool according to claim 3, wherein the at least one prong includes two prongs.

5. A dowel insertion tool according to claim 3, wherein in the advanced position, each of the two prongs defines a longitudinal axis which extends orthogonally to the longitudinal axis of the hollow sleeve.

6. A dowel insertion tool according to claim 3, wherein the actuator includes a rotatable knob positioned about the hollow sleeve.

7. A dowel insertion tool according to claim 6, wherein the rotatable knob includes an annular channel formed on an inner surface thereof and the elongated member includes a transverse extension positioned within the annular channel, and further including a cam slot formed in the first end of the hollow sleeve and a pin having one end fixedly connected to the rotatable knob and a second end positioned within the cam slot, wherein rotation of the rotatable knob causes the pin to move along the cam slot to move the rotatable knob axially about the hollow sleeve.

8. A dowel insertion tool according to claim 2, further including a guide member fastened to the second end of the hollow sleeve, the guide member having at least one guide bore, each guide bore being dimensioned and configured to slidably receive one of the at least one prong.

9. A dowel insertion tool according to claim 8, wherein the at least one guide bore includes two guide bores and the at least one prong includes two prongs.

10. A dowel insertion tool according to claim 8, further including a support plate operably connected to the second end of the elongated member, the support plate including a slot configured to slidably receive one end of the at least one prong, the other end of the at least one prong being slidably positioned within the at least one guide bore.

* * * * *